(12) United States Patent  
Miller et al.

(10) Patent No.: US 8,396,540 B2
(45) Date of Patent: Mar. 12, 2013

(54) ELECTRONIC FETAL MONITORING ASSESSMENT SYSTEM AND METHOD

(75) Inventors: Lisa A. Miller, Chicago, IL (US);
Cynthia L. Bell, Woodridge, IL (US);
Caren S. Busen, Timewell, IL (US);
Randall I. Paul, Brea, CA (US)

(73) Assignee: Clinical Computer Systems Incorporated, Elgin, IL (US)

( * ) Notice: Subject to any disclaimer, the term of this patent is extended or adjusted under 35 U.S.C. 154(b) by 1307 days.

(21) Appl. No.: 12/139,201

(22) Filed: Jun. 13, 2008

(65) Prior Publication Data

US 2009/0054797 A1   Feb. 26, 2009

Related U.S. Application Data

(60) Provisional application No. 60/934,330, filed on Jun. 13, 2007.

(51) Int. Cl.
*A61B 5/024* (2006.01)
(52) U.S. Cl. ........................................................ 600/511
(58) Field of Classification Search .................. 600/511
See application file for complete search history.

(56) References Cited

U.S. PATENT DOCUMENTS

| | | | | |
|---|---|---|---|---|
| 5,954,663 A * | 9/1999 | Gat | ............................... | 600/511 |
| 5,954,666 A * | 9/1999 | Snell | ............................. | 600/523 |
| 6,306,089 B1 * | 10/2001 | Coleman et al. | .............. | 600/437 |
| 6,907,284 B2 * | 6/2005 | Hamilton et al. | .............. | 600/511 |
| 2006/0052704 A1 * | 3/2006 | Baba et al. | ..................... | 600/453 |

\* cited by examiner

*Primary Examiner* — Niketa Patel
*Assistant Examiner* — Alyssa M Alter
(74) *Attorney, Agent, or Firm* — Pauley Petersen & Erickson (57) ABSTRACT

Electronic fetal monitoring assessment tools and methods of use thereof. The electronic fetal monitoring assessment tools are useable in connection with Electronic Fetal Monitoring ("EFM") systems, such as those EFM systems currently used by and available to medical professionals. Electronic fetal monitoring assessment tools may include an electronic measurement tool for one or more of assessing the baseline FHR, assessing variability of the baseline FHR, assessing decelerations in the FHR and/or assessing acceleration in the FHR. Electronic measurement tools may be used as electronically generated visual tools to assess one or more fetal heart rate patterns.

21 Claims, 7 Drawing Sheets

ELECTRONIC FETAL MONITORING ASSESSMENT SYSTEM AND METHOD

CROSS REFERENCE TO RELATED APPLICATION

This application claims the benefit of U.S. provisional patent application Ser. No. 60/934,330, filed on 13 Jun. 2007. This provisional patent application is hereby incorporated by reference herein in its entirety and is made a part hereof, including but not limited to those portions which specifically appear hereinafter.

BACKGROUND OF THE INVENTION

1. Field of the Invention

This invention relates generally to a system and a method of assessment of fetal heart rate patterns or values in connection with Electronic Fetal Monitoring ("EFM") systems and, more particularly, to one or more electronic measurement tools and the method of use thereof in connection with EFM systems.

2. Discussion of Related Art

EFM systems are generally used during labor and childbirth to provide medical professionals with fetal heart rate ("FHR") and uterine contraction tracings. These tracings are generally displayed on a monitor or similar display in the vicinity of the patient for viewing and use by attendant medical professionals. FHR and uterine contraction tracings are generally used by medical professionals to assess normal, abnormal and/or nonreassuring patterns and respond accordingly.

Various estimating techniques are used by medical professionals to assess patterns or values within EFM systems. Often such techniques are limited by the size or position of the display, the requirements or condition of the patient, the values of the tracings and other limitations.

There is an ongoing need for an improved system and method for assessment and interpretation of EFM information, including FHR patterns or signals.

SUMMARY OF THE INVENTION

An EFM assessment system and method according to the present invention provides various electronic fetal monitoring assessment tools to the medical professional for use in connection with existing EFM systems, particularly those that provide FHR and uterine contraction tracings.

According to one preferred embodiment of the invention, one or more tools may be used in connection with currently available EFM systems to provide additional or supplemental visual information to the medical professional. The tools of this invention can be selectably actuated to electronically overlay tracings of FHR and uterine contractions to visually indicate baselines and/or similar visual information usable to assist in the decision making process during labor and childbirth.

According to one embodiment of this invention, an electronic fetal monitoring assessment tool for use with an EFM system includes at least one sensor, a data processor in combination with the sensor(s) and a display in combination with the data processor. The sensor(s) are positionable on or about a patient to measure maternal uterine contraction information and fetal heart rate information. The data processor receives and processes the maternal contraction information and the fetal heart rate information from the sensor(s). The display visually communicates to a user the fetal heart rate information as a fetal heart rate tracing within a first coordinate structure and the maternal contraction information as a contraction line within a second coordinate structure. The first coordinate structure includes a plurality of vertical coordinates expressed as beats per minute and a plurality of horizontal coordinates expressed as seconds.

The electronic fetal monitoring assessment tool according to one embodiment of this invention includes at least one electronic measurement tool manually controlled by a user interface in combination with the EFM to place an electronically generated graphic indicator over the first coordinate structure or the second coordinate structure on the display. The electronically generated graphic indicator is preferably visible on the display when positioned over the first coordinate structure and/or the second coordinate structure to assist the user in assessment and/or interpretation of FHR information.

The electronic fetal monitoring assessment tool of this invention may include an electronic measurement tool for one or more of assessing the baseline FHR, assessing variability of the baseline FHR, assessing decelerations in the FHR and/or assessing accelerations in the FHR.

In one embodiment of this invention, the electronic measurement tool for assessing the baseline FHR provides a graphic indicator such as an electronically generated baseline of the fetal heart rate tracing. The electronic measurement tool may further include an information window electronically generated within the display and a coordination circuit. Upon placement of the electronically generated baseline within the first coordinate structure, the coordination circuit can determine a horizontal coordinate of the electronically generated baseline and output into the information window a corresponding baseline fetal heart rate value. The information window can further display a date and a time of the placement of the electronically generated baseline within the first coordinate structure. One or more graphic indicators of this invention can be used in combination with the baseline, the information window and the coordination circuit described above.

In another embodiment of this invention, the electronic measurement tool for assessing variability of the FHR provides a graphic indicator such as an electronically generated range window movably positionable over the fetal heart rate tracing and spanning at least one range of vertical coordinates of the first coordinate structure. In one embodiment, the range of vertical coordinates spans five beats per minute. In another embodiment, the range of vertical coordinates spans twenty-five beats per minute. The range window may span a range of horizontal coordinates of the first coordinate structure. In certain embodiments of this invention, the range of horizontal coordinates spans one minute.

In yet another embodiment of this invention, an electronic measurement tool for assessing decelerations of the FHR provides a graphic indicator having an electronically generated horizontal line segment with a first end positionable about a starting point of a deceleration event within the first coordinate structure and an opposing second end. The graphic indicator further includes a vertical line extending perpendicular to the horizontal line segment from the second end thereof. In one embodiment, the horizontal line segment spans a range of thirty seconds within the first coordinate structure and the vertical line extends from the first coordinate structure into the second coordinate structure.

In still another embodiment of this invention, the electronic measurement tool for assessing accelerations of the FHR provides a graphic indicator including the electronically generated baseline of the fetal heart rate tracing, as described above, in combination with an electronically generated first segment extending along the electronically generated baseline over a predetermined amount of horizontal coordinates, and an electronically generated second segment extending at an angle relative to the first segment over a predetermined amount of vertical coordinates. In one embodiment, the amount of horizontal coordinates is a range of fifteen seconds and the amount of vertical coordinates is a range of fifteen beats per minute. In another embodiment, the amount of horizontal coordinates is a range of ten seconds and the amount of vertical coordinates is a range of ten beats per minute. According to one embodiment of this invention, the graphic indicator further includes an electronically generated third segment positioned between the first segment and the second segment, such that the first segment, the second segment and the third segment form a triangular structure. The first segment, the second segment and the third segment (if present), desirably form a unit movable along the electronically generated baseline.

The present invention also contemplates a method of fetal monitoring assessment using one or more electronic measurement tools as described hereinabove. The method includes the step of acquiring maternal uterine contraction information and fetal heart rate information from a mother and/or a fetus through one or more sensors positioned on or about the mother and/or the fetus. The method further includes the step of displaying the fetal heart rate information as a fetal heart rate tracing within a first coordinate structure and the maternal uterine contraction information as a contraction line within a second coordinate structure. The method still further includes the steps of actuating a selectable electronic measurement tool based upon a user input, and displaying an electronically generated graphic indicator within the first coordinate structure and/or the second coordinate structure.

The present invention further contemplates a method of assessing a fetal heart rate pattern from fetal heart rate information displayed as a fetal heart rate tracing within a first coordinate structure and maternal contraction information displayed as a contraction line within a second coordinate structure on a display of an EFM system. The method generally includes the steps of a) selecting a graphic indicator from a computer-generated list of available graphic indicators, b) moving the selected graphic indicator relative to the fetal heart rate tracing and/or the contraction line to select a placement position for the graphic indicator within the first coordinate structure and/or the second coordinate structure, c) placing the selected graphic indicator in the selected placement position within the first coordinate structure and/or the second coordinate structure, and d) visually comparing the graphic indicator to the fetal heart rate tracing and/or the contraction line to assess the fetal heart rate pattern.

The invention further contemplates software on a recordable medium and executable on a data processor (e.g., EFM machine) for implementing the tools and methods of this invention.

Other advantages will be apparent to those skilled in the art from the following detailed description taken in conjunction with the drawings.

DESCRIPTION OF THE INVENTION

The present invention provides electronic fetal monitoring assessment tools and methods of use thereof. The electronic fetal monitoring assessment tools of this invention are useable in connection with Electronic Fetal Monitoring ("EFM") systems, such as those EFM systems currently used by and available to medical professionals.

Those skilled in the art and following the teachings herein provided will appreciate that while the descriptions below of various electronic fetal monitoring assessment tools of this invention include preferred colors or configurations, such colors or configurations are used for illustrative purposes only and may be modified as appropriate, depending on need.

Figure 1:
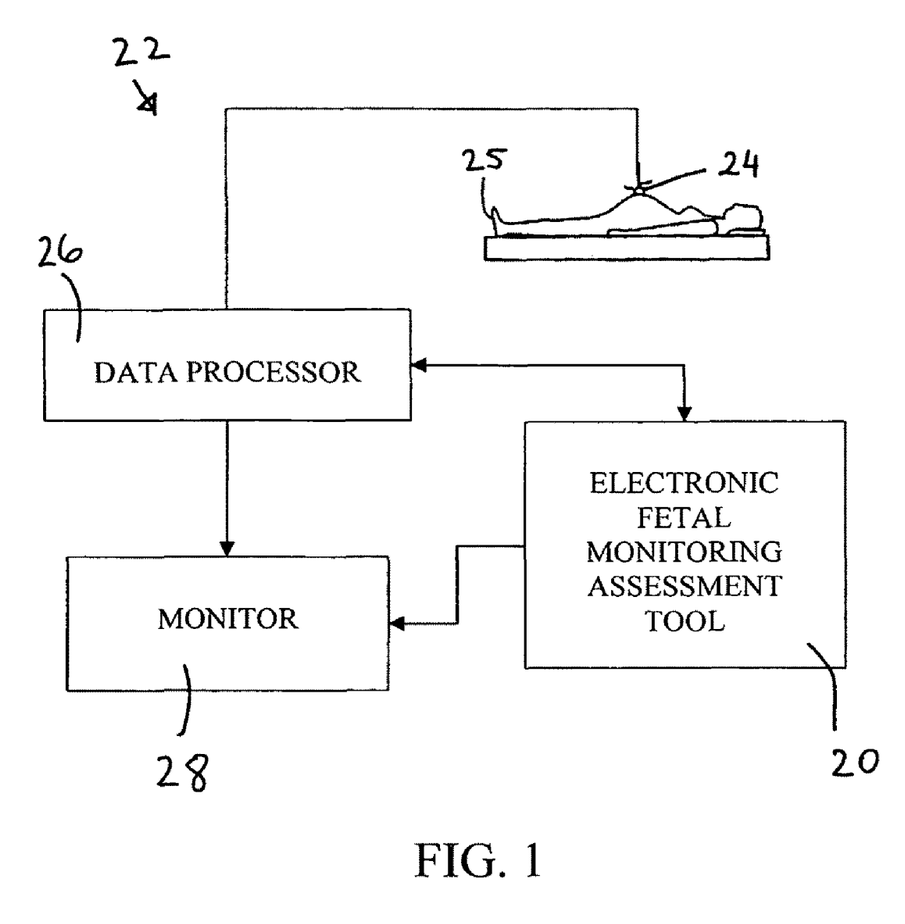
FIG. 1 is a diagrammatic representation illustrating an electronic fetal monitoring assessment tool and EFM system of one embodiment of this invention.

FIG. 1 diagramatically illustrates an electronic fetal monitoring assessment tool 20 according to one embodiment of this invention in connection with a representative EFM system 22. The EFM system 22 of FIG. 1 includes at least one sensor 24 positionable on or about patient 25 for the purpose of gathering maternal uterine contraction information and fetal heart rate information. Typically, in instances where the measure of fetal heart motion is desired, the sensor(s) 24 are placed upon the abdomen of the patient mother. Suitable sensors for gathering data points on fetal heart rate and uterine contractions are currently used and well known. The sensor(s) 24 can be a single sensor or an array of sensors. As an example, a first sensor may acquire maternal uterine contraction information and a second sensor may acquire fetal heart rate information. Alternatively, a single sensor may be used to acquire both maternal uterine contraction information and fetal heart rate information.

Data collected by sensor(s) 24 are sent to a data processing unit of the EFM system, shown in FIG. 1 as data processor 26. The data processor 26 receives and processes the maternal contraction information and the fetal heart rate information to obtain the desired readable output, which is ultimately displayed to the user. In one embodiment of this invention, data processor 26 includes a signal acquisition circuit, a signal analysis circuit, a memory circuit and a display circuit. The term "circuit" as used herein broadly refers to hardware, software, or combination of hardware and software which performs or enables the described function.

In one embodiment, a signal acquisition circuit preferably obtains motion data corresponding to maternal contractions and/or fetal heart beats from the one or more sensors 24. The data acquired by the signal acquisition circuit is relayed to a signal analysis circuit, for processing. A memory circuit is provided to store data, both acquired by the acquisition circuit and processed by the analysis circuit. Data stored in the memory circuit may be accessed and retrieved by the display circuit, for display, and/or the signal analysis circuit, for analysis. The memory circuit can be considered optional in EFM systems that print-out a paper copy of the output in real-time. The display circuit is preferably connected to an electronic display, such as monitor 28, for displaying the obtained data in user readable format, such as an X-Y coordinate structure discussed below. The EFM system 22 may also desirably be connected to a printer through the display circuit.

Figure 2:
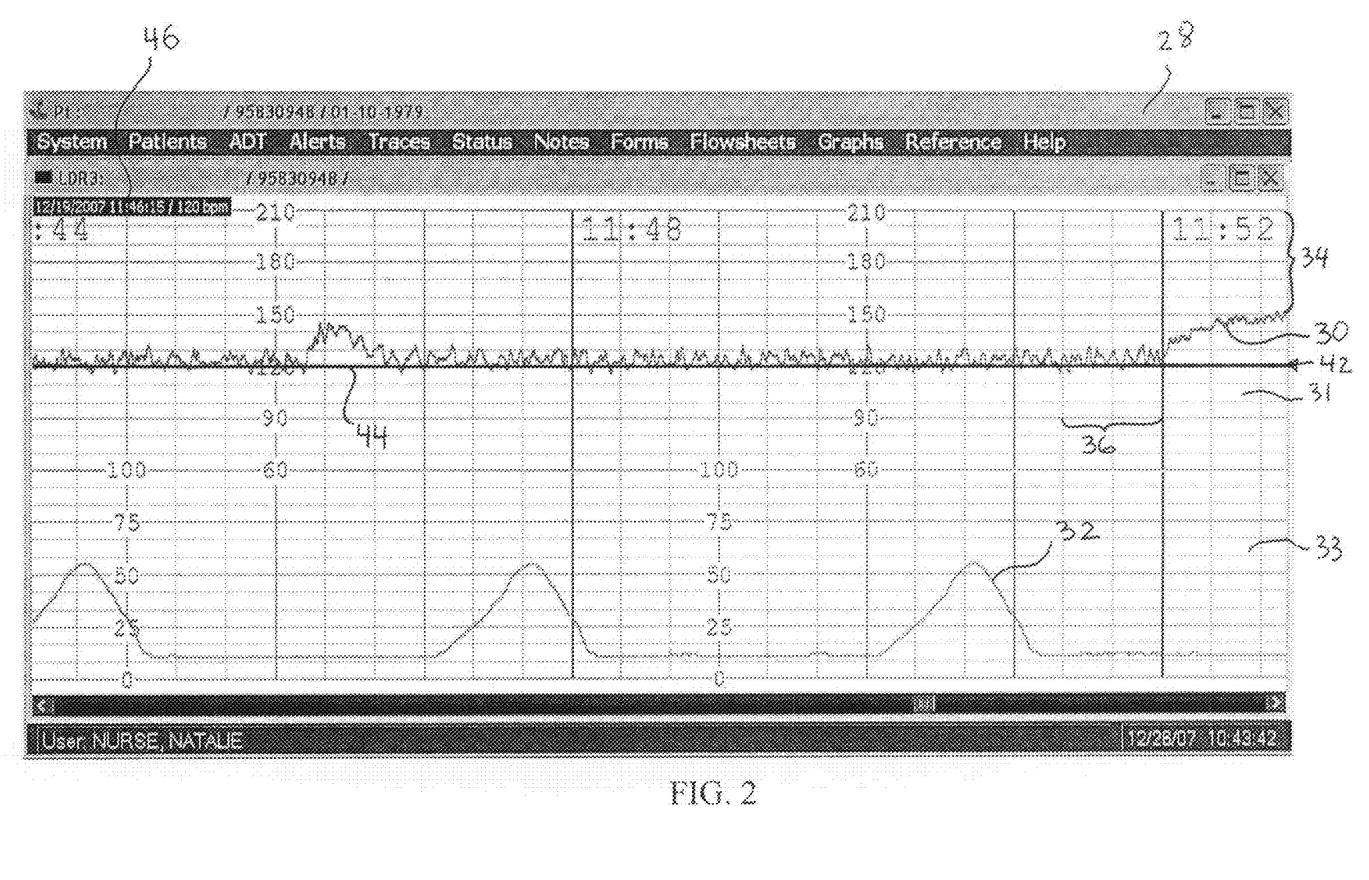
FIG. 2 is a screen shot of an EFM display, showing an electronic measurement tool for assessing the baseline FHR according to one embodiment of this invention.

FIGS. 2-7 illustrate exemplary display screens produced by the EFM system 22 and shown to the user through monitor 28. As shown in FIG. 2, monitor 28 typically and desirably visually communicates to the user both fetal heart rate information through a fetal heart rate tracing 30 and maternal contraction information as contraction line 32. The fetal heart rate tracing 30 is plotted within first coordinate structure 31 and contraction line 32 is plotted within second coordinate structure 33. First coordinate structure 31 is an X-Y plot having vertical coordinates 34 representing beats per minute and the horizontal coordinates 36 representing units of time, e.g., seconds. Such coordinate structures for fetal heart rate monitoring and maternal contractions are commonly used in current EFM systems.

According to one embodiment, electronic fetal monitoring assessment tool 20 of this invention provides at least one electronic measurement tool 40 manually implemented and controlled by a user interface, for example, and without limitation, a mouse or a keyboard, in combination with EFM system 22. The manually controlled electronic measurement tool 40 allows a user to place electronically generated graphic indicator 42 over first coordinate structure 31 and/or second coordinate structure 33 on display 28. Electronically generated graphic indicator 42 is preferably visible on display 28 when positioned over first coordinate structure 31 and/or second coordinate structure 33. Electronic fetal monitoring assessment tool 20 may include an electronic measurement tool for one or more of assessing the baseline FHR, assessing variability of the baseline FHR, assessing decelerations in the FHR and/or assessing acceleration in the FHR.

In one embodiment of this invention, electronic fetal monitoring assessment tool 20 provides electronic measurement tool 40 for assessing the baseline FHR, and, as shown in FIG. 2, electronically generated graphic indicator 42 is electronically generated baseline 44 over fetal heart rate tracing 30.

The current National Institute of Child Health and Human Development ("NICHD") guidelines for interpretation of fetal heart rate tracings recommend the assessment of baseline FHR over a minimum window of 10 minutes. The normal baseline FHR range is typically between about 110 and about 160 beats per minute ("bpm"). The baseline FHR is typically reported as a single number describing the mean FHR rounded to the nearest increment of 5 bpm (i.e., 140 or 145 vs. 142 or 144), excluding any segments of baseline FHR that differ by more than 25 bpm, any periods of marked FHR variability and any periodic or episodic changes. Fetal bradycardia is generally determined if the baseline FHR is below 110 bpm, and fetal tachycardia is generally determined if the baseline FHR is above 160 bpm.

According to one embodiment of this invention, shown in FIG. 2, electronically generated baseline 44 is an electronically generated horizontal line movably positionable over fetal heart rate tracing 30 to determine the baseline fetal heart rate value. Electronically generated baseline 44 may be red or may have any other suitable color that preferably distinguishes the electronically generated baseline 44 on display 28.

According to one embodiment of this invention, electronic measurement tool 40 for assessing the baseline FHR further includes information window 46 electronically generated within display 28 and a coordination circuit (not shown). Upon placement of electronically generated baseline 44 within first coordinate structure 31, the coordination circuit preferably determines a horizontal coordinate of electronically generated baseline 44 and outputs a corresponding baseline fetal heart rate value into information window 46. The baseline fetal heart rate value may be rounded to the nearest increment of 5 bpm or may be otherwise expressed as desired or required. Information window 46 may further display a date and a time of the placement of electronically generated baseline 44 within first coordinate structure 31. Information window 46 may be a pop-up window, a display box positioned within display 28 of EFM system 22, or a designated area within display 28 for displaying FHR-related information. In one embodiment of this invention, information window 46 appears within display 28 of EFM system 22 after the placement of electronically generated baseline 44 within first coordinate structure 31. In other words, the placement of electronically generated baseline 44 within first coordinate structure 31 preferably actuates electronic generation of information window 46 on display 28.

A user, such as a clinician or a nurse, may activate electronic measurement tool 40 for assessing the baseline FHR by, for example, actuating (e.g. clicking a mouse) a cursor positioned within first coordinate structure 31 or second coordinate structure 33 and selecting the appropriate graphic indicator from a computer-generated list. Alternatively, or additionally, a user may activate electronic measurement tool 40 for assessing the baseline FHR by opening a computer-generated menu of available electronic measurement tools and/or graphic tools and selecting the desired graphic indicator. One or more electronic measurement tools of this invention may be activated in a similar fashion.

Upon selection of the electronically generated baseline graphic indicator, electronically generated baseline 44 is preferably generated on display 28. The user may movably position electronically generated baseline 44 within first coordinate structure 31. The user may select a placement position for electronically generated baseline 44 and place electronically generated baseline 44 at the identified placement position. The placement position preferably generally corresponds with the baseline FHR identified by the user. Once electronically generated baseline 44 is placed into position, the coordination circuit preferably determines a horizontal coordinate of electronically generated baseline 44 and determines a corresponding baseline fetal heart rate value rounded to the nearest five beats per minute. Expressing the baseline fetal heart rate value in increments of 5 beats per minute can desirably be a required function to prevent error by requiring the user to follow the NICHD guidelines. Information window 46 may be electronically generated on display 28 to display the fetal heart rate value as well as the time and date of the placement of electronically generated baseline 44 within first coordinate structure 31. Information window 46 may be displayed in the upper left-hand corner of display 28, as shown in FIG. 2, or other suitable location on display 28.

The EFM can be optionally connected to a medical database for saving or transferring notes, interpretations and/or observations directly into a patient's medical record.

One or more electronic fetal monitoring assessment tools of this invention may be used to assess variability of the baseline FHR. Baseline variability is generally defined as fluctuations in the FHR of two cycles per minute or greater.

Baseline variability is visually quantified as the amplitude in bpm from peak to trough. Absent variability is typically defined as undetectable. Minimal variability is typically defined as greater than undetectable but less than or equal to 5 bpm. Moderate variability is typically defined as 6-25 bpm. Marked variability is typically defined as greater than 25 bpm.

Figure 3:
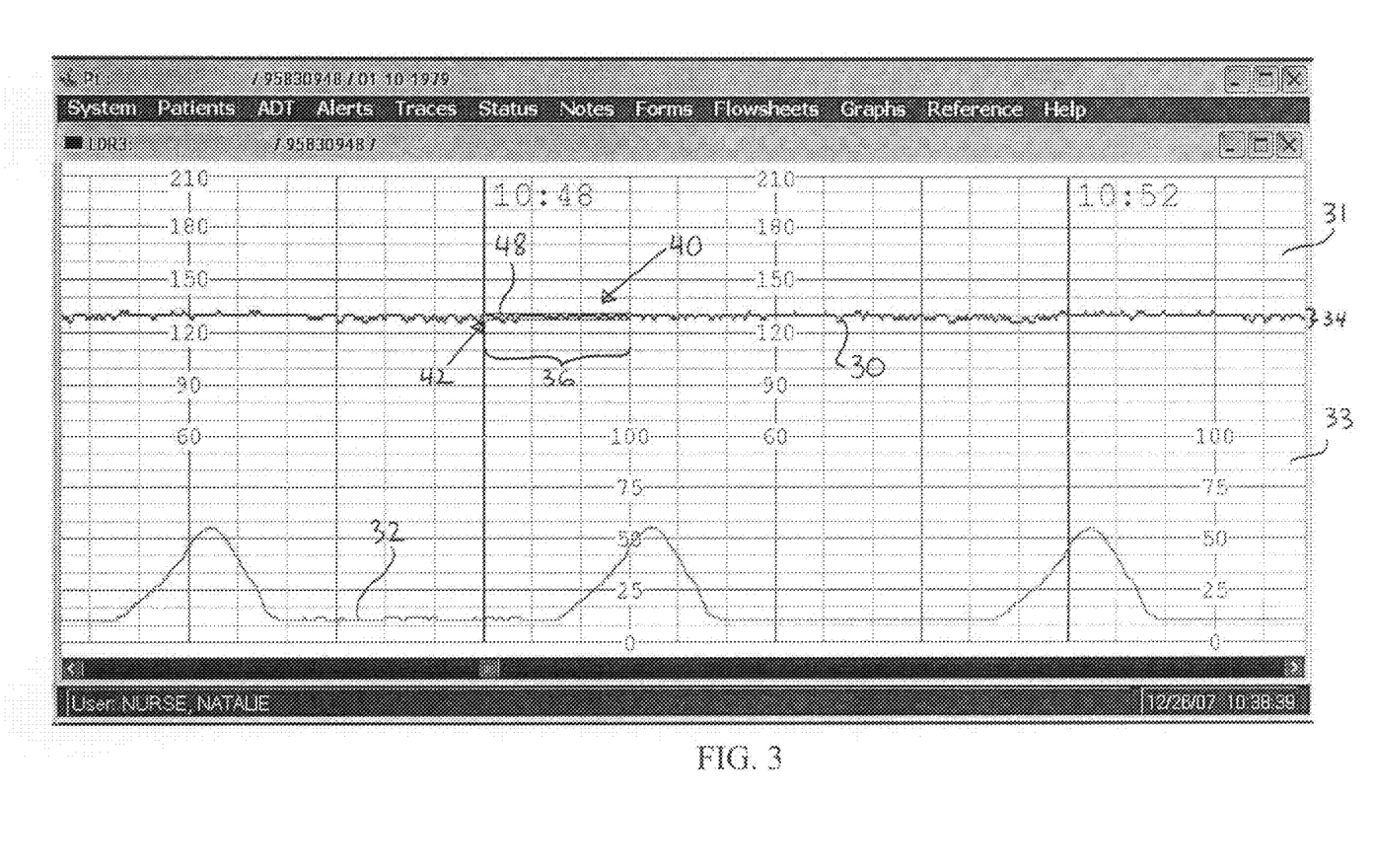
FIG. 3 is a screen shot of an EFM display, showing an electronic measurement tool for assessing variability of the baseline FHR according to one embodiment of this invention.

According to another embodiment of this invention, as shown in FIG. 3, electronic fetal monitoring assessment tool 20 includes electronic measurement tool 40 for assessing variability of the baseline FHR and electronically generated graphic indicator 42 includes electronically generated range window 48. Electronically generated range window 48 is movably positionable over fetal heart rate tracing 30 and preferably spans at least one range of vertical coordinates 34 of first coordinate structure 31. In one embodiment, shown in FIG. 3, electronically generated range window 48 spans the range of vertical coordinates 34 equal to five beats per minute. In another embodiment, shown in FIG. 4, electronically generated range window 48 spans the range of vertical coordinates 34 equal to twenty-five beats per minute.

Figure 4:
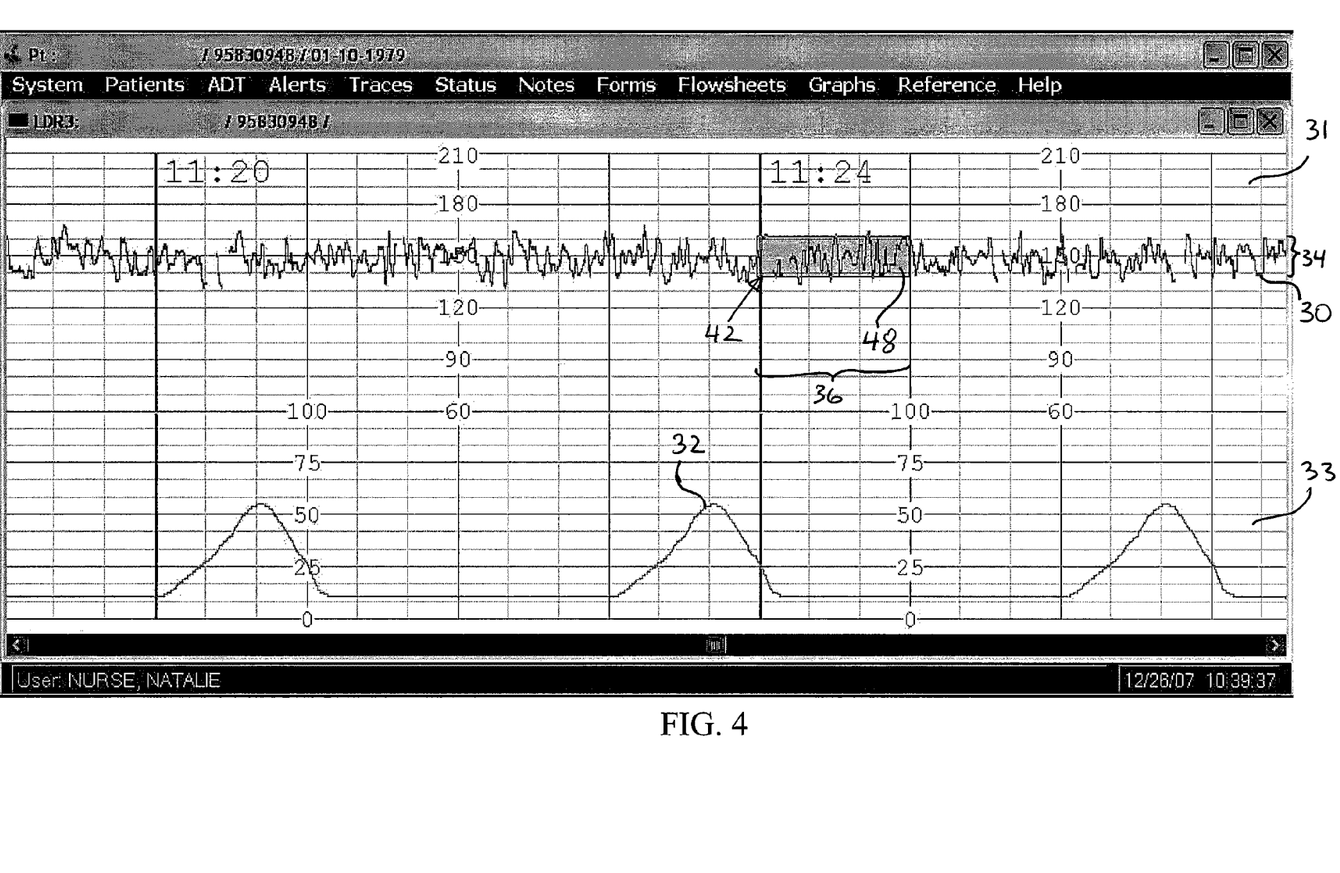
FIG. 4 is a screen shot of an EFM display, showing an electronic measurement tool for assessing variability of the baseline FHR according to another embodiment of this invention.

In certain embodiments, as shown in FIGS. 3 and 4, electronically generated range window 48 spans a range of horizontal coordinates 36 of first coordinate structure 31. In the embodiments shown in FIGS. 3 and 4, electronically generated range window 48 spans the range of horizontal coordinates 36 equal to one minute within first coordinate structure 31.

In one embodiment, as shown in FIG. 3, electronically generated graphic indicator 42 for assessing variability of the baseline FHR includes electronically generated range window 48 covering a range of vertical coordinates 34 spanning 5 bpm and a range of horizontal coordinates 36 spanning one minute. Electronically generated range window 48 may be visualized on display 28 as a magenta-shaded rectangle having a vertical width of 5 bpm and a horizontal length of one minute. The 5 bpm electronically generated range window 48 may be movably positionable over fetal heart rate tracing 30 and/or the baseline FHR to determine if variability is absent or minimal. Should the variability be more than minimal, the user would then use the 25 bpm electronically generated range window (see below).

In one embodiment, as shown in FIG. 4, electronically generated graphic indicator 42 for assessing variability of the baseline FHR includes electronically generated range window 48 covering a range of vertical coordinates 34 spanning 25 bpm and a range of horizontal coordinates 36 spanning one minute. Electronically generated range window 48 may be visualized on display 28 as a magenta-shaded rectangle having a vertical width of 25 bpm and a horizontal length of one minute. The 25 bpm electronically generated range window 48 may be movably positionable over fetal heart rate tracing 30 and/or the baseline FHR to determine if variability is moderate or marked.

The 5 bpm and 25 bpm electronically generated range windows, alone or in combination, allow the user to determine which of the four variability definitions to use. The 5 bpm electronically generated range window allows the clinician to determine if the variability is absent or minimal and chart in the notes as appropriate. The 25 bpm electronically generated range window allows the clinician to determine if the variability is moderate or marked and chart in the notes as appropriate.

One or more electronic fetal monitoring assessment tools of this invention can be used by a medical professional to assess decelerations of the FHR. Decelerations of the FHR are generally defined as periodic (occurring associated with contractions) or episodic (occurring without an association to contractions). Periodic decelerations may be described as recurrent if they occur with 50% or greater of the contractions in a given 20 minute period.

The onset to nadir of a deceleration may be either abrupt (less than thirty seconds) or gradual (thirty seconds or greater). This determination is crucial to identifying the type of deceleration (early, late, variable, or prolonged). Decelerations may be further quantified by the depth of the nadir in bpm and by the time from onset to offset.

Early deceleration is typically defined as a gradual decrease and return to baseline associated with a contraction. The onset, nadir, and offset occur coincidentally with the contraction, with the nadir of the deceleration occurring at the peak of the contraction.

Late deceleration is typically defined as a gradual decrease and return to baseline associated with a contraction. Onset is delayed, with the nadir of deceleration occurring after the peak of the contraction.

Variable deceleration is typically defined as an abrupt decrease in FHR of 15 bpm or more, lasting 15 seconds or more, but less than 2 minutes. Variable deceleration may be periodic or episodic. When associated with uterine contractions (periodic), variable decelerations may vary in onset, depth, and duration from contraction to contraction.

Prolonged deceleration is typically defined as a gradual or abrupt decrease of 15 bpm or more, lasting 2 minutes or more, but less than 10 minutes. Prolonged deceleration may be periodic or episodic.

Figure 5:
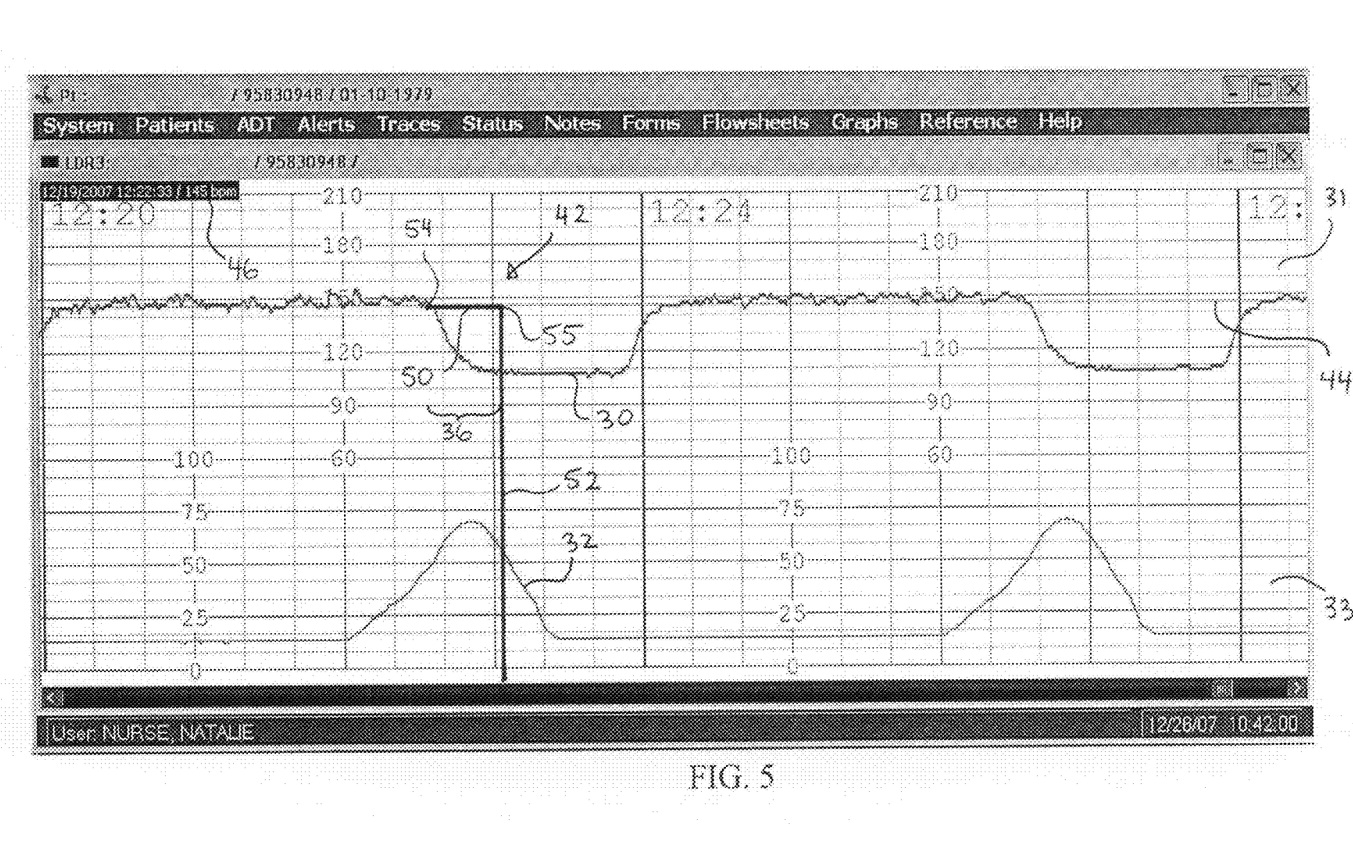
FIG. 5 is a screen shot of an EFM display, showing an electronic measurement tool for assessing decelerations in the FHR according to one embodiment of this invention.

According to another embodiment of this invention, electronic fetal monitoring assessment tool 20 includes electronic measurement tool 40 for assessing deceleration of the FHR and, as shown in FIG. 5, electronically generated graphic indicator 42 includes electronically generated horizontal line segment 50 and electronically generated vertical line 52 extending perpendicular with respect to horizontal line segment 50. Horizontal line segment 50 has first end 54 positionable about a starting point of a deceleration event within first coordinate structure 31. Horizontal line segment 50 has second end 55, opposite first end 54, and electronically generated vertical line 52 extends from second end 55 of horizontal line segment 50. In one embodiment, horizontal line segment 50 extends along a range of thirty seconds within first coordinate structure 31. In the embodiment shown in FIG. 5, first coordinate structure 31 is aligned in parallel with second coordinate structure 33 and electronically generated vertical line 52 extends from first coordinate structure 31 into second coordinate structure 33. Electronically generated vertical line 52 may cross the entire vertical height of second coordinate structure 33, as shown in FIG. 5.

In one embodiment of this invention, horizontal line segment 50 is thirty seconds in horizontal length, allowing the clinician to accurately differentiate between gradual versus abrupt deceleration when evaluating onset to nadir, which is a key determination in identifying the type of deceleration. The clinician places the first end 54 of horizontal line segment 50 on or about the starting point of the deceleration event and evaluates the onset to nadir by comparing the nadir to vertical line 52, which represents the second time frame. If the nadir is to the left of vertical line 52, it is less than thirty seconds, and the deceleration can be qualified as abrupt. If the nadir is at or to the right of vertical line 52, it is equal to or greater than thirty seconds, and the deceleration can be qualified as gradual. Vertical line 52 may preferably assist the clinician in evaluation of nadir of deceleration as it relates to the peak of uterine contraction, to differentiate between early versus late decelerations.

After the clinician opens the deceleration graphic indicator and determines the length of the deceleration from onset to nadir, the clinician can open the notes and chart the findings. The clinician can also determine the relationship of the deceleration to the contraction and chart the deceleration accordingly in the notes.

One or more electronic fetal monitoring assessment tools of this invention may be used to assess accelerations in the FHR. Acceleration of FHR is generally defined as a visual apparent increase (onset of acceleration to peak is reached in less than thirty seconds) in the FHR from the most recently calculated baseline. The duration of an acceleration is defined as the time from the initial change in the FHR from the baseline to the return of the FHR to the baseline. Accelerations are generally defined for gestations of 32 weeks and greater to have an acme greater than or equal to 15 bpm above the baseline, and the onset to offset of the acceleration of 15 seconds or more. Accelerations are generally defined for gestations of less than 32 weeks to have an acme greater than or equal to 10 bpm above the baseline, and the onset to offset of the acceleration of 10 seconds or more.

Figure 6:
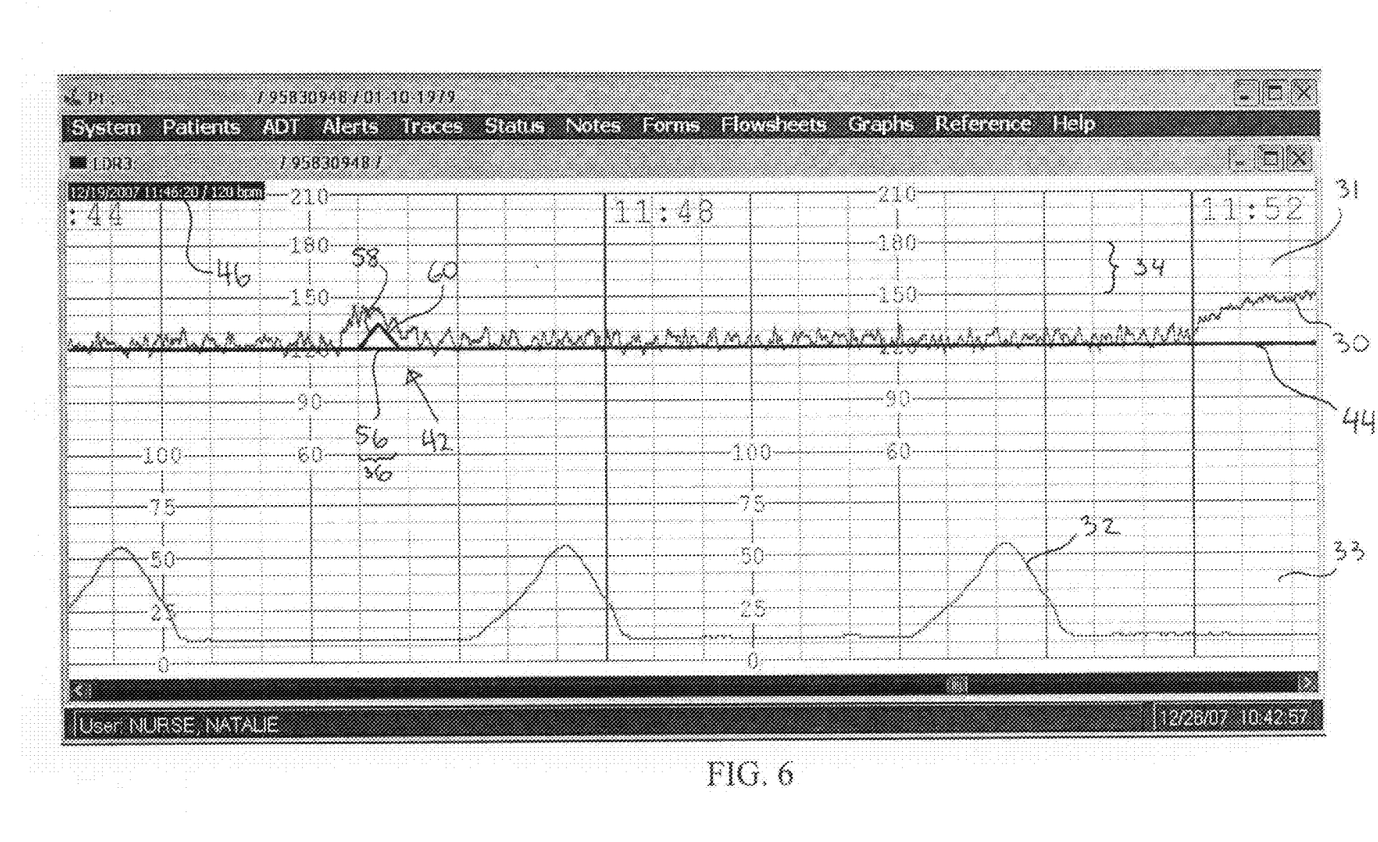
FIG. 6 is a screen shot of an EFM display, showing an electronic measurement tool for assessing accelerations in the FHR according to one embodiment of this invention.
Figure 7:
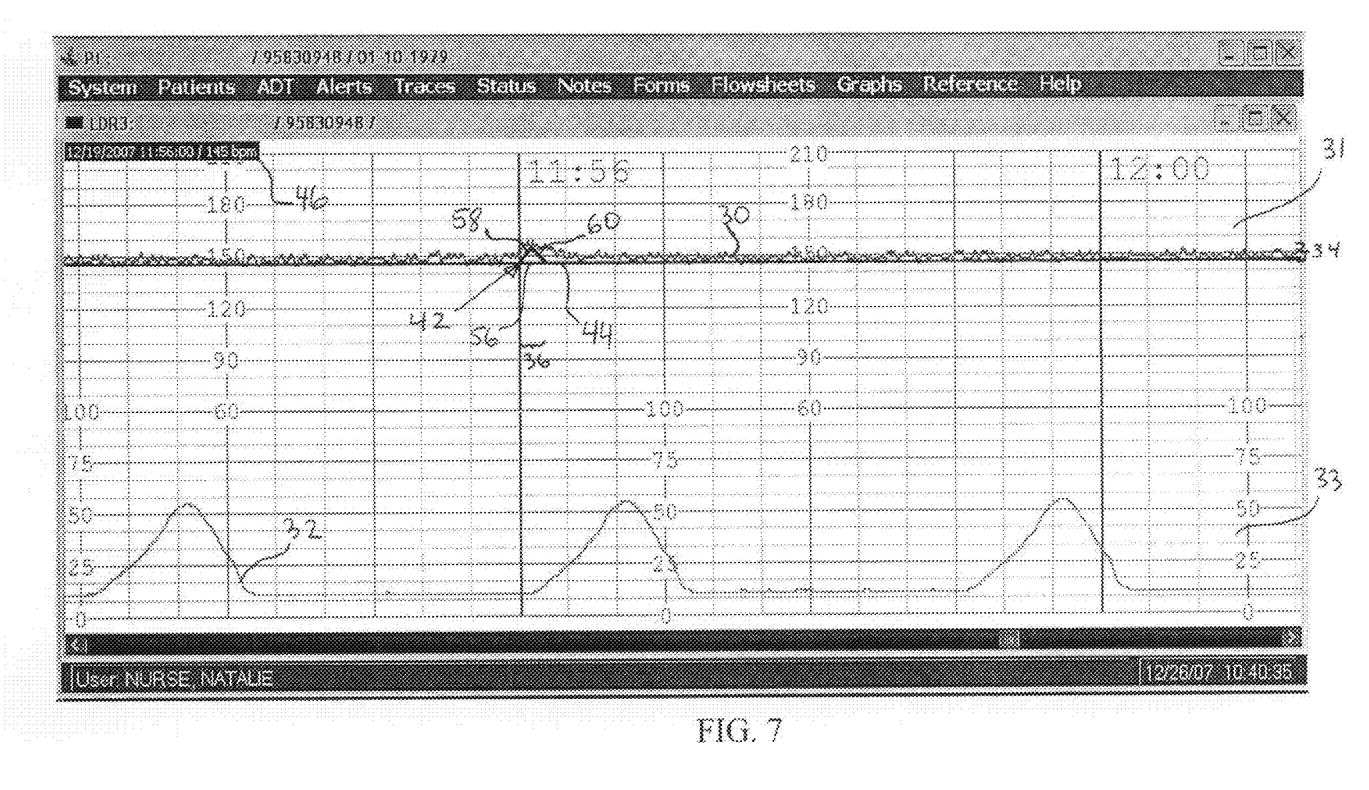
FIG. 7 is a screen shot of an EFM display, showing an electronic measurement tool for assessing accelerations in the FHR according to another embodiment of this invention.

According to certain embodiments of this invention, the electronic fetal monitoring assessment tool includes electronic measurement tool 40 for assessing accelerations in the FHR and, such as shown in FIGS. 6 and 7, the electronically generated graphic indicator 42 includes electronically generated baseline 44 of the fetal heart rate. As shown in FIGS. 6 and 7, the electronically generated graphic indicator 42 further includes electronically generated first segment 56 extending along electronically generated baseline 44 of fetal heart rate tracing 30 over a predetermined amount of horizontal coordinates, and electronically generated second segment 58 extending at an angle relative to first segment 56 over a predetermined amount of vertical coordinates. In one embodiment, shown in FIG. 6, the amount of horizontal coordinates spans a range of fifteen seconds and the amount of vertical coordinates spans a range of fifteen beats per minute (15×15 tool). In another embodiment, as shown in FIG. 7, the amount of horizontal coordinates spans a range of ten seconds and the amount of vertical coordinates spans a range of ten beats per minute (10×10 tool). The first segment 56 and the second segment 58 may form a unit that is movable along the electronically generated baseline 44.

In certain embodiments, the electronically generated graphic indicator 42 further includes electronically generated third segment 60 positioned between first segment 56 and second segment 58. First segment 56, second segment 58 and third segment 60 may be arranged as shown in FIG. 6 to form a triangle. The first segment 56, the second segment 58 and the third segment 60 may form a unit that is movable along the electronically generated baseline 44.

In one embodiment of this invention, as shown in FIG. 6, the electronically generated graphic indicator 42 for assessing acceleration of FHR may include electronically generated baseline 44 and electronically generated first segment 56, electronically generated second segment 58 and electronically generated third segment 60 forming a triangle having an altitude of 15 bpm and a base of 15 seconds (15×15 tool). In another embodiment of this invention, as shown in FIG. 7, the triangle may have an altitude of 10 bpm and a base of 10 seconds (10×10 tool). First segment 56 forms the base of the triangle and desirably overlays a portion of the electronically generated baseline 44. The clinician may activate the electronically generated graphic indicator by, for example, actuating (e.g., clicking a mouse) a cursor positioned within first coordinate structure 31 or second coordinate structure 33 and selecting the graphic indicator for assessing acceleration from a computer-generated list. The clinician may then place the electronically generated graphic indicator on fetal heart rate tracing 30 and compare the acceleration with the electronically generated graphic indicator (i.e., the 10×10 tool or the 15×15 tool, as described above). If the acceleration matches or exceeds the parameters of the graphic indicator, the clinician may determine that the acceleration meets the defined criteria.

For gestations of less than 32 weeks, the clinician may preferably use the 10×10 acceleration tool, as described above. For gestations of 32 weeks or more, the clinician may preferably use the 15×15 acceleration tool, as described above.

After the 10×10 or 15×15 acceleration tool is actuated, the corresponding electronically generated graphical indicator 42 will appear on display 28. The clinician may then movably position the electronically generated baseline 44 over the baseline of fetal heart rate tracing 30 and the unit formed by the first segment 56, the second segment 58, and the third segment 60, over the acceleration to be evaluated. When the baseline is determined by the coordination circuit, the baseline fetal heart rate value may be displayed within information window 46, preferably, but not necessarily, in increments of 5 bpm (i.e., 140 or 145 vs. 142 or 144). The clinician may slide the unit formed by the first segment 56, the second segment 58, and the third segment 60, along the fixed electronically generated baseline 44 to the acceleration to be evaluated. Utilizing this tool, the clinician is preferably able to determine if the acceleration meets the definition of greater than 15 bpm and lasting longer than 15 seconds for a gestation of 32 weeks or greater, or if the acceleration meets the definition of greater than 10 bpm and lasting longer than 10 seconds for a gestation of less than 32 weeks.

The present invention also contemplates a method of fetal monitoring assessment using one or more electronic measurement tools as described hereinabove. The method includes the step of acquiring maternal uterine contraction information and fetal heart rate information from a mother and/or a fetus trough one or more sensors positioned on or about the mother and/or the fetus. The method further includes the step of displaying the fetal heart rate information as a fetal heart rate tracing within a first coordinate structure and the maternal uterine contraction information as a contraction line within a second coordinate structure. The method still further includes the steps of actuating a selectable electronic measurement tool based upon a user input, and displaying an electronically generated graphic indicator within the first coordinate structure and/or the second coordinate structure.

The present invention further contemplates a method of assessing a fetal heart rate pattern from fetal heart rate information displayed as a fetal heart rate tracing within a first coordinate structure and maternal contraction information displayed as a contraction line within a second coordinate structure on a display of an EFM system. The method generally includes the steps of a) selecting a graphic indicator from a computer-generated list of available graphic indicators, b) moving the selected graphic indicator on the fetal heart rate tracing and/or the contraction line to select a placement position for the graphic indicator within the first coordinate structure and/or the second coordinate structure, c) placing the selected graphic indicator in the selected placement position within the first coordinate structure and/or the second coordinate structure, and d) visually comparing the graphic indicator to the fetal heart rate tracing and/or the contraction line to assess the fetal heart rate pattern.

The invention illustratively disclosed herein suitably may be practiced in the absence of any element, part, step, component, or ingredient, which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An electronic fetal monitoring assessment tool for use with an Electronic Fetal Monitoring (EFM) system including:
    at least one sensor positionable on or about a patient to measure maternal uterine contraction information and fetal heart rate information;
    a data processor in combination with the at least one sensor to receive and process the maternal contraction information and the fetal heart rate information from the at least one sensor;
    a display in combination with the data processor, wherein the display visually communicates to a user the fetal heart rate information as a fetal heart rate tracing within a first coordinate structure and the maternal contraction information as a contraction line within a second coordinate structure, wherein the first coordinate structure comprises a plurality of vertical coordinates expressed as beats per minute and a plurality of horizontal coordinates expressed as seconds;
    the electronic fetal monitoring assessment tool comprising data processor executable instructions on a readable medium of the EFM, the instructions operating at least one electronic measurement tool that is manually selected using a user interface in combination with the EFM to automatically generate an electronically generated graphic indicator that is manually placed within the first coordinate structure or second coordinate structure on the display, wherein the electronically generated graphic indicator is visible on the display when positioned within the first coordinate structure or second coordinate structure, and the graphic indicator comprises an electronically generated range window movably positionable over the fetal heart rate tracing and spanning at least one range of vertical coordinates of the first coordinate structure, the electronically generated range window comprising a first window of a first vertical coordinate range spanning five beats per minute and a second window of a second vertical coordinate range spanning twenty-five beats per minute, wherein the first window is visually distinguishable from the second window.

2. The electronic fetal monitoring assessment tool of claim 1, further comprising a second electronic measurement tool including a further graphic indicator comprising an electronically generated baseline of the fetal heart rate tracing.

3. The electronic fetal monitoring assessment tool of claim 2, further comprising:
    an information window electronically generated within the display; and
    a coordination circuit, whereupon placement of the electronically generated baseline within the first coordinate structure, the coordination circuit determines a horizontal coordinate of the electronically generated baseline and outputs into the information window a corresponding baseline fetal heart rate value.

4. The electronic fetal monitoring assessment tool of claim 3, wherein the information window displays a date and a time of the placement of the electronically generated baseline within the first coordinate structure.

5. The electronic fetal monitoring assessment tool of claim 2, wherein the further graphic indicator further comprises:
    an electronically generated first segment extending along the electronically generated baseline of the fetal heart rate tracing over a predetermined amount of horizontal coordinates; and
    an electronically generated second segment extending at an angle relative to the first segment over a predetermined amount of vertical coordinates.

6. The electronic fetal monitoring assessment tool of claim 5, wherein the amount of horizontal coordinates comprises a range of fifteen seconds and the amount of vertical coordinates comprises a range of fifteen beats per minute.

7. The electronic fetal monitoring assessment tool of claim 5, wherein the amount of horizontal coordinates comprises a range of ten seconds and the amount of vertical coordinates comprises a range of ten beats per minute.

8. The electronic fetal monitoring assessment tool of claim 5, wherein the further graphic indicator further comprises an electronically generated third segment positioned between the first segment and the second segment, wherein the first segment, the second segment and the third segment form a triangular structure.

9. The electronic fetal monitoring assessment tool of claim 1, further comprising a second electronic measurement tool including a further graphic indicator comprising:
    a horizontal line segment having a first end positionable about a starting point of a deceleration event within the first coordinate structure and an opposing second end; and
    a vertical line extending perpendicular to the horizontal line segment from the second end of the horizontal line segment.

10. The electronic fetal monitoring assessment tool of claim 9, wherein the first coordinate structure is aligned in parallel with the second coordinate structure and the vertical line extends from the first coordinate structure into the second coordinate structure.

11. A method of fetal monitoring assessment using an electronic measurement tool, the method comprising the steps of:
    acquiring maternal uterine contraction information and fetal heart rate information;
    displaying the fetal heart rate information as a fetal heart rate tracing within a first coordinate structure and the maternal uterine contraction information as a contraction line within a second coordinate structure;
    generating a selectable electronic fetal heart rate deceleration assessment tool based upon a user input, the selectable electronic fetal heart rate deceleration assessment tool including a first electronically generated graphic indicator comprising a horizontal line segment having an unconnected first end to be positioned at a deceleration starting point on a fetal heart rate tracing and a second end connected to a vertical line segment extending in a direction of a deceleration of the fetal heart rate tracing;
    positioning the selectable electronic fetal heart rate deceleration assessment tool within the first coordinate structure in response to further user positioning input;
    displaying the first electronically generated graphic indicator within the first coordinate structure;

generating a selectable electronic fetal heart rate acceleration measurement tool based upon a user input, the selectable electronic fetal heart rate acceleration measurement tool including a second electronically generated graphic indicator comprising a horizontal first line segment and a second line segment extending at a non-perpendicular angle from the first line segment in a direction of an acceleration of the fetal heart rate tracing;

positioning the selectable electronic fetal heart rate acceleration measurement tool within the first coordinate structure in response to further user positioning input; and displaying the second electronically generated graphic indicator within the first coordinate structure.

12. An electronic fetal monitoring assessment tool for use with an Electronic Fetal Monitoring (EFM) system including:

at least one sensor positionable on or about a patient to measure maternal uterine contraction information and fetal heart rate information;

a data processor in combination with the at least one sensor to receive and process the maternal contraction information and the fetal heart rate information from the at least one sensor;

a display in combination with the data processor, wherein the display visually communicates to a user the fetal heart rate information as a fetal heart rate tracing within a first coordinate structure and the maternal contraction information as a contraction line within a second coordinate structure, wherein the first coordinate structure comprises a plurality of vertical coordinates expressed as beats per minute and a plurality of horizontal coordinates expressed as seconds;

the electronic fetal monitoring assessment tool comprising: data processor executable instructions on a readable medium of the EFM, the instructions operating electronic measurement tools that are each manually controlled by a user interface in combination with the EFM to place an electronically generated graphic indicator within the first coordinate structure or second coordinate structure on the display, wherein the electronically generated graphic indicator is visible on the display when positioned within the first coordinate structure or second coordinate structure, a first of the electronic measurement tools comprising a fetal heart rate deceleration assessment tool including a first electronically generated graphic indicator comprising a horizontal line segment having an unconnected first end to be positioned at a deceleration starting point on a fetal heart rate tracing and a second end connected to a vertical line segment extending in a direction of a deceleration of the fetal heart rate tracing; and a second of the electronic measurement tools comprising a fetal heart rate acceleration assessment tool including a second electronically generated graphic indicator comprising a horizontal first line segment and a second line segment extending at a non-perpendicular angle from the first line segment in a direction of an acceleration of the fetal heart rate tracing.

13. The electronic fetal monitoring assessment tool of claim 12, wherein the horizontal line segment of the fetal heart rate deceleration assessment tool spans a range of thirty seconds within the first coordinate structure.

14. The electronic fetal monitoring assessment tool of claim 12, wherein the first coordinate structure is aligned in parallel with the second coordinate structure and the vertical line segment extends from the first coordinate structure into the second coordinate structure.

15. The electronic fetal monitoring assessment tool of claim 12, wherein the horizontal first line segment of the fetal heart rate acceleration assessment tool extends along the electronically generated baseline of the fetal heart rate tracing over a predetermined amount of horizontal coordinates.

16. The electronic fetal monitoring assessment tool of claim 15, wherein the predetermined amount of horizontal coordinates comprises a range of fifteen seconds, and the second line segment comprises a vertical coordinate range of fifteen beats per minute.

17. The electronic fetal monitoring assessment tool of claim 15, wherein the predetermined amount of horizontal coordinates comprises a range of ten seconds, and the second line segment comprises a vertical coordinate range of ten beats per minute.

18. The electronic fetal monitoring assessment tool of claim 15, wherein the fetal heart rate acceleration assessment tool comprises an electronically generated third line segment extending between the first line segment and the second line segment, wherein the first line segment, the second line segment and the third line segment form a triangular structure.

19. The electronic fetal monitoring assessment tool of claim 18, wherein the first segment, the second segment and the third segment form a unit movable along an electronically generated baseline.

20. The electronic fetal monitoring assessment tool of claim 1, wherein the electronically generated range window comprises a shaded rectangle.

21. The electronic fetal monitoring assessment tool of claim 1, wherein the electronically generated range window spans a range of horizontal coordinates of one minute.

* * * * *